United States Patent [19]

Ogusu et al.

[11] Patent Number: 5,202,114

[45] Date of Patent: Apr. 13, 1993

[54] GEL COMPOSITION AND NAIL POLISH

[75] Inventors: Yoshiyuki Ogusu, Tokyo; Yoshikazu Soyama, Zami; Makoto Takahashi; Tooru Okamoto, both of Yokohama; Masaaki Ishiwatari; Motokiyo Nakano, both of Sagamihara, all of Japan

[73] Assignee: Shiseido Company, Ltd., Tokyo, Japan

[21] Appl. No.: 526,108

[22] Filed: Feb. 22, 1990

[30] Foreign Application Priority Data

Jun. 24, 1988 [JP] Japan .................. 63-154622

[51] Int. Cl.$^5$ .................. A61K 7/04; A61K 7/043
[52] U.S. Cl. .................. 424/61; 106/499
[58] Field of Search .................. 424/61

[56] References Cited

U.S. PATENT DOCUMENTS

| 3,864,294 | 2/1975 | Busch, Jr. | 424/61 |
| 4,345,080 | 8/1982 | Bolich, Jr. | 424/70 |
| 4,409,203 | 10/1983 | Gordon et al. | 424/61 |
| 4,421,902 | 12/1983 | Chang | 424/81 |
| 4,545,981 | 10/1985 | Jacquet | 424/61 |
| 4,740,370 | 5/1988 | Faryniarz | 424/61 |
| 4,832,944 | 5/1989 | Socci | 424/61 |
| 4,954,619 | 9/1990 | Lang | 424/61 |

OTHER PUBLICATIONS

Remz, Cosmetics and Toiletries, vol. 103, Dec. 1988 pp. 70-82.

Primary Examiner—Thurman K. Page
Assistant Examiner—James M. Spear
Attorney, Agent, or Firm—Wenderoth, Lind & Ponack

[57] ABSTRACT

A gel composition or a nail polish comprising at least one cationic surfactant having a propylene oxide chain and/or an ethylene oxide chain, an organic modified clay mineral and a solvent. Addition of the specific cationic surfactant maintains the good thixotropy due to the organic modified clay mineral and restricts the change in viscosity with time and with a slight change in the content of the organic modified clay mineral to a very narrow range.

8 Claims, 2 Drawing Sheets

MEASUREMENT CONDITION
BL-type VISCOMETER
ROTOR No.3 12rpm

GEL COMPOSITION AND NAIL POLISH

This application is a continuation-in-part of International Application No. PCT/JP89/00627, filed Jun. 23, 1989 in the Japanese Patent Office as receiving office and designating the United States.

BACKGROUND OF THE INVENTION

1. Field of the Invention

The present invention relates to a gel composition and a nail polish, and more particularly, to the improvement of the age stability thereof.

2. Description of the Prior Art

Nail polishes and coatings, etc., are produced by dispersing powders of a pigment, a pearl pigment, etc. in solvents. Such powders do not have such good solubility as to preclude a possibility of separating from the solvent and precipitating in the container during long-term storage. As a countermeasure, when a nail polish or a coating is conventionally produced by dispersing a powder in a solvent, a gel composition containing an organic modified clay mineral obtained by modifying the clay mineral by an organic solvent so as to allow the clay mineral to swell and an organic solvent is first produced and a pigment and the like is mixed with the gel composition.

The gel composition composed of a clay mineral is ready to change into a fluid sol by stirring and gelates again when it is allowed to stand. In other words, the gel composition has thixotrophy.

In this way, a conventional nail polish utilizes the good thixotropy derived from the clay mineral. That is, the nail polish is stored in a gel state so as to prevent the precipitation of the powders of a pigment and the like, while it is shaken together with the container for use so as to facilitate application.

Mere addition of such an organic modified clay mineral to a nail polish, however, cannot provide a sufficient stability and precipitation of the powders and a change in viscosity are sometimes experienced.

SUMMARY OF THE INVENTION

Accordingly, it is an object of the present invention to eliminate the above-described problems in the prior art and to provide a gel composition and a nail polish having both good thixotropy and age stability. As a result of studies undertaken by the present inventors to achieve this aim, it has been found that a specific cationic surfactant is capable of providing good dispersion and viscosity stability without impairing the thixotropy derived from an organic modified clay mineral. The present invention has been achieved on the basis of this finding.

The gel composition of the principle invention of the present invention is characterized by containing at least one cationic surfactant having a propylene oxide chain(-hereinunder referred to as "PO chain") and/or an ethylene oxide chain (hereinunder referred to as "EO chain"), an organic modified clay mineral and a solvent.

The gel composition of the present invention in a first aspect is characterized by additionally containing a powder.

The gel composition of the present invention in second aspect is characterized by further containing an anionic surfactant.

The gel composition of the present invention in a still further third aspect is characterized by additionally containing nitrocellulose.

The nail polish of the present invention in a further aspect is characterized by containing at least one cationic surfactant having a propylene oxide chain and/or an ethylene oxide chain, an organic modified clay mineral, a solvent and a pigment.

The structure of the present invention will be described in more detail hereinunder.

Cationic surfactant having PO chain and/or EO chain

A cationic surfactant having a PO chain and/or an EO chain used in the present invention is exemplified by surfactants represented by the following general formulas:

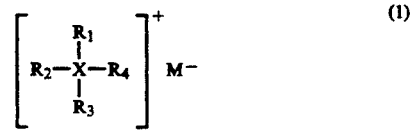

wherein X represents nitrogen or phosphorus, Y is sulfur, M— is chlorine ion, bromine ion, iodine ion, nitrous acid ion, hydroxyl ion, acetic acid ion, methyl sulfate ion or a combination thereof, $R_1$ is a hydrocarbon group having 1 to 30 carbon atoms with or without a substituent, and at least one of $R_2$, $R_3$ and $R_4$ represents a hydrocarbon group having 1 to 30 carbon atoms and a PO chain and/or an EO chain with or without hydrogen or a substituent at the end of the hydrocarbon group, the other(s) of $R_2$, $R_3$ and $R_4$ representing hydrocarbon group or groups having 1 to 30 carbon atoms with or without the same or different substituents. The number of addition moles of the PO chain and/or the EO chain is preferably 1 to 50 more preferably 9 to 40.

The content of the cationic surfactant having a PO chain and/or an EO chain used in the present invention is preferably 0.01 to 40 wt %, more preferably 0.05 to 15 wt %, in the total amount of gel composition. If it is less than 0.01 wt %, the dispersibility of a clay mineral is poor, thereby making it impossible to provide good thixotropy. On the other hand if it exceeds 40 wt %, the clay mineral is apt to agglomerate during long-term storage.

The content of the cationic surfactant having a PO chain and/or an EO chain used in the present invention is preferably 0.01 to 10 wt %, more preferably 0.05 to 5 wt % in the total amount of nail polish if each of the gel compositions in the further aspect of the invention is a nail polish. If it is less than 0.01 wt %, the dispersibility of a clay mineral is poor, thereby making it impossible to provide good thixotropy. On the other hand, if it exceeds 10 wt %, the clay mineral is apt to agglomerate during long-term storage.

The content of the cationic surfactant having a PO chain and/or and EO chain used in the present invention is preferably 0.01 to 10 wt %, more preferably 0.02 to 3 wt % in the total amount of coating if each of the gel compositions in the second and third aspects of the invention is a coating. If it is less than 0.01 wt %, the dispersibility of a clay mineral is poor, thereby making it impossible to provide good thixotropy. On the other hand, if it exceeds 10 wt %, the clay mineral is apt to agglomerate during long-term storage.

Organic Modified Clay Mineral

As an example of a clay mineral which is used as the material of the organic modified clay mineral in the present invention will be cited a water-swelling clay mineral which is one of the colloidal hydrated aluminum silicates having a three-layered structure, for example, a natural or synthetic smectite such as montmorillonite, saponite and hectorite. Exchangeable cations existing between the crystal layers of such a clay mineral are substituted by organic polar compounds or organic cations to produce an organic polar compounds or organic cations to produce an organic modified clay mineral. As an example of the organic cation, a quaternary ammonium salt type cation surfactant will be cited. The quaternary ammonium salt type cation surfactant is exemplified by those represented by the following general formula:

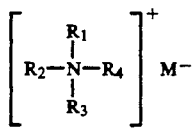

wherein $R_1$ represents an alkyl group having 10 to 22 carbon atoms or a benzyl group, $R_2$ a methyl group or an alkyl group having 10 to 22 carbon atoms, $R_3$ and $R_4$ represent an alkyl group having 1 to 3 carbon atoms or a hydroxyalkyl group, and M is a halogen atom or a methyl sulfate residue or the like.

For example, they are dodecyltrimethylammonium chloride, tetradecyltrimethylammonium chloride, hexadecyltrimethylammonium chloride, octadecyltrimethylammonium chloride, arachiltrimethylammonium chloride, ditetradecyldimethylammonium chloride, dihexadecyldimethylammonium chloride, dioctadecyldimethylammonium chloride, benzyltetradecyldimethylammonium chloride, benzylhexadecyldimethylammonium chloride, benzyloctadecyldimethylammonium chloride, bromides corresponding thereto and dihexadecylpropylethylammonium methyl sulfate.

Any given one or more of these organic cations are selected as occasion demands.

An organic modified clay mineral is produced by, for example, dissolving the above-described cationic surfactant in ion-exchanged water, adding a clay mineral to the aqueous solution, dispersing, filtering out and drying the clay mineral.

Among the thus-obtained organic modified clay minerals, dioctadecyldimethylammonium salt modified montmorillonite, benzyloctadecyldimethylammonium salt modified montmorillonite and dihexadecyldimethylammonium salt modified montmorillonite are preferable. As a commercially available organic modified clay mineral, Benton 27, 28 (produced by National Red Co., Inc.) will be cited. Any given one or more of these minerals are selected as occasion demands.

The content of the organic modified clay mineral used in the present invention is preferably 1 to 20 wt %, more preferably 4 to 15 wt % in the total amount of gel composition. If it is less than 1 wt %, it is impossible to provide good thixotropy. On the other hand, if it exceed 20 wt %, it is difficult to stir the homogeneous dispersion in the production of the gel composition.

The mixing ratio of the organic modified clay mineral and the cationic surfactant having a PO chain or an EO chain is very important for producing the advantage of the present invention. The preferred mixing ratio of the cationic surfactant having a PO chain or an EO chain with the organic modified clay mineral is about 1/15 to 2 times. If it is less than 1/15, it is impossible to maintain a good age stability. If it exceeds 2 times, not only is a good age stability not obtained but also if the gel composition is used as a nail polish, it is disadvantageously apt to peel off the nail.

All the interaction between these two components is not clear, but it may be considered that the cationic surfactant having a PO chain or an EO chain acts on the surface of the organic modified clay mineral. A part of the quaternary ammonium salt type cationic surfactant between the layers of the organic modified clay mineral is substituted by a cationic surfactant having a PO chain of an EO chain.

Accordingly, the organic modified clay mineral in the present invention includes an organic modified clay mineral with a cationic surfactant having a PO chain or an EO chain caught in the layer thereof.

The content of the organic modified clay mineral used in the present invention is preferably 0.05 to 10 wt %, more preferably 0.1 to 5 wt %, in the total amount of nail polish if each of the gel compositions in the further aspects of the invention is a nail polish. If it is less than 0.05 wt %, it is impossible to provide good thixotropy. On the other hand, if it exceeds 10 wt %, the gloss and the wearability (resistance to peeling) are deteriorated.

The content of the organic modified clay mineral used in the present invention is preferably 0.05 to 10 wt %, more preferably 0.1 to 3 wt % in the total amount of coating if each of the gel compositions in the further aspects of the invention is a coating. If it is less than 0.05 wt %, it is impossible to provide good thixotropy. On the other hand, if it exceeds 10 wt % the gloss and the wearability (resistance to peeling) are deteriorated.

Solvent

As the solvent in the present invention, toluene, xylene; benzene; acetic acid esters such as n-butyl acetate, isobutyl acetate and ethyl acetate; ketones such as methylethyl ketone and acetone; alcohols such as n butanol, isopropyl alcohol and ethyl alcohol; cellosolves such as methyl cellosolve, butyl cellosolve, phenyl cellosolve and benzyl cellosolve; and carbitols such as methyl carbitol and butyl carbitol are usable. Any given one or more of these solvents are selected as occasion demands.

The content of the solvent used in the present invention is preferably 30 to 99 wt %, more preferably 60 to 96 wt % in the total amount of gel composition. If it is less than 30 wt %, the solid content is too high for good dispersion to obtain a good gel composition.

The content of the solvent used in the present invention is preferably 50 to 90 wt %, more preferably 60 to 80 wt % in the total amount of nail polish if each of the gel compositions in the further aspects of the invention is a nail polish. If it is less than 50 wt %, it is impossible to provide good application properties. On the other hand, if it exceeds 90 wt %, the gloss and the wearability (resistance to peeling) are deteriorated.

The content of the solvent used in the present invention is preferably 30 to 70 wt %, more preferably 40 to 65 wt % in the total amount of coating if each of the gel compositions in the further aspects of the invention is a coating. If it is less than 30 wt %, it is impossible to provide good application properties. On the other hand, if it exceeds 70 wt %, the gloss and the wearability (resistance to peeling) are deteriorated.

Powder

As the powder used in the gel composition in the further aspects of the invention of the present invention, any powder ordinarily mixed with a nail polish and coating may be used.

For example, at least one selected from the group consisting of the following pigments is usable: inorganic powders such as talk, kaolin, sericite, commonmica, synthetic mica, phlogopite, lepidolite, biotite, lithia mica, vermiculite, magnesium carbonate, calcium carbonate, diatomaceous earth, magnesium silicate, calcium silicate, aluminium silicate, barium silicate, barium sulfate, strontium silicate, metal salt of tungstic acid, silica, hydroxy apatite, zeolite, boron nitrate and ceramic powder; organic powders such as nylon powder, polyethylene powder, benzoguanamine powder, ethylene tetrafluoride powder, styrene divinylbenzene copolymer powder, distyrene benzene, pinhole polymer powder and crystallite cellulose; inorganic white pigments such as titanium oxide, iron oxide (red iron oxide) and iron titanate; inorganic brown pigments such as γ-iron oxide, inorganic yellow pigments such as yellow iron oxide and loess; inorganic black pigments such as black iron oxide and carbon black; inorganic violet pigments such as mango violet and cobalt violet; inorganic green pigments such as chromium oxide, chromium hydroxide and cobalt titanate; inorganic blue pigments such as ultramarine and Prussian blue; pearl pigments such as titanium oxide coated bismus oxychloride, bismus oxychloride, titanium oxide coated talk, pearlessence, colored titanium oxide coated mica; clay mineral such as Bentone; metal powder pigments such as aluminum powder and copper powder; organic pigments such as Red #201, Red #202, Red #204, Red #205, Red #220, Red #226, Red #228, Red #405, Orange #203, Orange #204, Yellow #205, Yellow #401 and Blue #404; organic pigments obtained by reacting pigments such as Red #3, Red #104, Red #106, Red #227, Red #230, Red #401, Red #505, Orange #205, Yellow #4, Yellow #5, Yellow #202, Yellow #203, Green #3 and Blue #1 with zirconium, barium or aluminum lake; natural dyes such as chlorophyll and β-carotene; magnesium oxide; magnesium hydroxide, calcium oxide, calcium hydroxide; aluminum oxide; aluminum hydroxide; silica; iron hydroxide; titanium dioxide; lower titanium oxide; zirconium oxide; chromium oxide; chromium hydroxide; manganese oxide; cobalt oxide; nickel oxide; iron titanate; cobalt titanate; and cobalt aluminate.

The preferred content of the powder is different depending upon the purpose of use of the gel composition, but it is ordinarily 0.001 to 30 wt % in the total amount of gel compound.

Anionic surfactant

Further addition of an anionic surfactant greatly enhances the age stability of the gel composition of the present invention. The anionic surfactant may be selected from a wide range of substances which are soluble or dispersible in an organic solvent. The typical anionic surfactants are phosphoric acid esters, carboxylic acids, sulfonic acids, and sulfuric acid esters.

As examples of the sulfuric acid esters, the esters represented by the following formulas (3) to (5) will be cited:

(3)

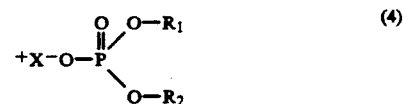

(4)

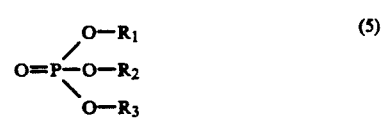

(5)

wherein $R_1$, $R_2$ and $R_3$ represent hydrocarbon groups having 1 to 30 carbon atoms with or without the same or different substituents, or the same or different hydrocarbon groups at least one of which is a hydrocarbon group having 1 to 30 carbon atoms and a PO chain and/o an EO chain with or without hydrogen or a substituent at the end of the hydrocarbon group.

The number of addition moles of a PO chain or an EO chain, if any, is preferably 1 to 50, more preferably 1 to 20.

The carboxylic acids are, for example, ether carboxylic acids such as polyoxyethylenemyristyl ether carboxylic acid and polyoxyethylenecetyl ether carboxylic acid and N-acyl sarcosines such as lauroylsarcocines and palmitoylsarcocines.

Examples of the sulfonic acids are dialkylsulfosuccinic acids such as dioctylsulfosuccinic acid, di-2-ethylhexylsulfosuccinic acid and di-n-hexylsulfosuccinic acid and alkylallylsulfonic acids such as laurylbenzenesulfonic acid and myristylbenzenesulfonic acid.

As examples of sulfuric acid esters, alkylsulfuric acid esters such as myristylsulfuric acid ester and cetyl sulfuric acid ester, POE cetyl ether sulfuric acid ester and POE nonylphenyl ether sulfuric acid ester will be cited and these may be used in the form of either acid or salt. The salt is selected from the group consisting of alkali metal salts, alkali earth metal salts, ammonia and organic amine salts. These salts are obtained by combining the sulfuric acids with, for example, hydrogen, lithium, sodium, potassium, magnesium, calcium, barium, ammonia and organic amines such as ethanol amine, diethanol amine, triethanol amine or a combination thereof. Any given one or more of these anionic surfactants are selected as occasion demands.

The content of the anionic surfactant used in the present invention is preferably 0.001 to 5 wt % in the total amount of nail polish if the gel composition further containing an anionic surfactant is a nail polish. If it is less than 0.001 wt %, it is difficult to maintain a good age stability for a long time. On the other hand, if it exceeds 5 wt %, the wearability (resistance to peeling) is deteriorated.

The content of the anionic surfactant has a close relationship with a cationic surfactant having a PO chain or an EO chain, and it is impossible to obtain good action without assuming the presence of the cationic surfactant. The preferred mixing ratio of the anionic surfactant with the cationic surfactant is about 1/10 to ½ time.

The content of the anionic surfactant used in the present invention is preferably 0.001 to 5 wt %, more preferably 0.001 to 2 wt %, in the total amount of coating if the gel composition further containing an anionic surfactant is a coating. If it less than 0.001 wt %, it is difficult to maintain a good age stability for a long time. On the other hand, if it exceeds 5 wt %, the wearability (resistance to peeling) is deteriorated.

Other ingredients

The gel composition of the present invention can be utilized in the form of a nail polish or a coating either as it is or by adding other ingredients thereto. The examples of other ingredients are a film forming material such as nitrocellulose ½ sec., nitrocellulose ¼ sec., nitrocellulose ⅛ sec. and nitrocellulose 1/16 sec.; a resin such as alkyd resins, acrylic resins, polyestel resins, sucrose resins, sulfonamid resins, rosin resins, phenol resins, amino resins and epoxy resins; a plasticizer such as dibutyl phthalate, dioctyl phthalate, tributyl citrate, acetyltributyl citrate, acetyltriethyl citrate and camphor; and other additives such as solvent, ultraviolet absorber, humectant, pharmaceutical, perfume and water-soluble ingredient. It goes without saying that these additives must be used under the qualitative and quantitative conditions which do not impair the objects of the present invention.

The structure which has been described above ensures the prevention of the deterioration such as the precipitation of the powder of the gel compositions described in the principle and first aspect of the present invention. The gel composition further containing an anionic surfactant of the present invention is advantageous in that the addition of an anionic surfactant further improves the age stability.

A method adopted for producing the gel composition of the present invention comprises the steps of, for example, dipping the chips obtained by rolling a mixture of an organic modified clay mineral, a nitrocellulose and a plasticizer by a two-stage heating rolling mill into a solvent so as to swell the chips, dispersing the chips sufficiently, mixing a specific amount of cationic surfactant having a PO chain and/or an EO chain therewith, thereby obtaining a gel composition, mixing a powder or a powder and other ingredients with the gel composition, and stirring the mixture. A method may also be adopted of dipping the chips obtained by rolling a mixture of an organic modified clay mineral, a nitrocellulose and a plasticizer by a two-stage heating roll into a solvent so as to swell the chips, dispersing the chips sufficiently, thereby obtaining a gel composition, mixing a specific amount of cationic surfactant having a PO chain and/or an EO chain therewith, thereby obtaining a gel composition, and mixing a cationic surfactant having a PO chain and/or an EO chain and a powder, and further other ingredients, if necessary, with the gel composition.

A nail polish further containing nitrocellulose of the present invention is advantageous in excellent age stability as the gel compositions claimed in the principle and the first and second aspects of the invention and it can be produced by the same method as those described above.

The gel compositions of the present invention are advantageous in that they can be utilized in the form of a nail polish or a coating having excellent age stability either as they are or by adding other ingredients thereto.

The above and other objects, features and advantages of the present invention will become clear form the following description of the preferred embodiments thereof, taken in conjunction with the accompanying drawings.

DESCRIPTION OF THE PREFERRED EMBODIMENTS

The present invention will be explained in detail hereinunder with reference to the following examples. It is to be understood that the present invention is not restricted to those examples. The mixing amount in the examples is expressed by wt %.

The methods for testing various properties of the compositions obtained will first be described.

Thixotropy or gel property

The thixotropy and gel property of this kind of composition are generally evaluated by the interlaminar distance of a clay mineral measured by X-rays. In the examples of the present invention, this method was also adopted. In the case of quaternary ammonium salt modified organic montmorillonite, the interlaminar distance is about 18.4 Å in powder state, and when the interlaminar distance of the gel composition was not less than 40 Å, the thixotropy or gel property was considered to be good.

Age stability

A nail polish or a coating is charged into a container and the precipitation and the separation were observed with the naked eye.
⊚: No precipitation nor separation was observed.
○: Slight precipitation and separation were observed.
□: Precipitation and separation were observed.
△: Much precipitation and separation were observed.

Gloss of coating film

The gloss of the coating film was evaluated by sensory examination in the actual use of a polish nail and a coating.
⊚: Very glossy
○: Comparatively glossy
□: Slightly glossy
△: Scarcely glossy
X: No gloss

Wearability(resistance to peeling)

(1) In the case of nail polish

A nail polish was actually applied to the nails and three days after, the wearability was evaluated by sensory examination.

⊚: Good state
◯: Comparatively good state
☐: Slightly bad state
Δ: Bad state
X: Very bad state (2) In the case of coating The wearability of coating after 6-month use was evaluated by sensory examination.

⊚: Good state
◯: Comparatively good state
☐: Slightly bad state
Δ: Bad state
X: Very bad state

EXAMPLES 1 TO 8

The influence of a cationic surfactant exerted on the interlaminar distance of an organic modified clay mineral was first examined.

Figure 1A:
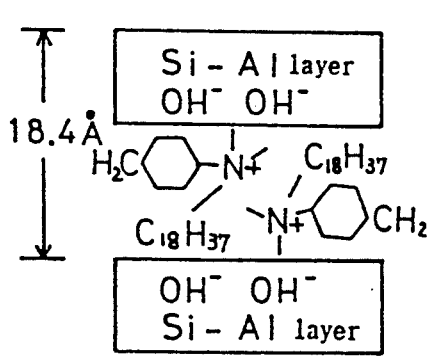
FIG. 1(A) is an explanatory view of the structure of an organic modified clay mineral with exchangeable cation between the layers substituted by a quaternary ammonium salt type cationic surfactant.
Figure 1B:
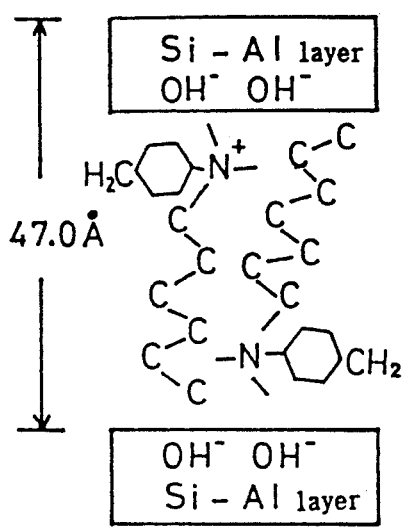
FIG. 1(B) shows that the interlaminer distance is increased when the organic modified clay mineral was dispersed in a solvent.

A clay mineral has a laminar structure and is charged between each of the Si and Al layers by isomorphous substitution or the like. In this state, although a polar solvent can penetrate between the layers, the ingress of a non-polar solvent such as an organic solvent is difficult. To solve this problem, the exchangeable cation between the layers was substituted by a quaternary ammonium salt type cationic surfactant, as shown in FIG. 1(A). The result was that the ingress of an organic solvent between the Si and Al layers was enabled. It was observed that in the case of such an organic modified clay mineral with exchangeable cation between the layers substituted by a quaternary ammonium salt type cationic surfactant, the interlaminar distance was about 18.4 Å in the absence of a solvent, and the interlaminar distance was increased to not less than 40 Å when the organic modified clay mineral was dispersed in a solvent such as toluene, as shown in FIG. 1 (B).

In the way, the thixotropy of an organic modified clay mineral is produced when an organic solvent has penetrated between the layers, thereby swelling the organic modified clay mineral.

However, a cationic surfactant having a PO chain or an EO chain has a too marked tendency of non-polarity to be used for organic modification of a clay mineral. No increase in the interlaminar distance of a clay mineral was observed which had intentionally been treated with the cationic surfactant having a PO chain or an EO chain and dispersed in a solvent such as toluene.

The present inventors investigated on the influence of the coexistence of a cationic surfactant having a propylene oxide or the like with an organic modified clay mineral on the interlaminar distance.

The gel compositions of the principle invention having the respective compositions shown in Table 1 were produced by ordinary method using a two-stage rolling mill and the interlaminar distance of the organic modified clay mineral of each gel composition was obtained.

TABLE 1

|  | EXAMPLES |  |  |  |  |  |  |  |
|---|---|---|---|---|---|---|---|---|
|  | 1 | 2 | 3 | 4 | 5 | 6 | 7 | 8 |
| Benzyloctadecyldimetyl ammonium salt modified montmorillonite | 15 | 15 | 15 | 15 | 10 | 10 | 10 | 10 |
| Cationic surfactant A | 15 | 15 | 15 | 15 | 10 | 10 | 10 | 10 |
| Dipolyoxy(2)myristyl ether phosphoric acid | — | 8 | — | 8 | — | 5 | — | 5 |
| n-butylacetate | 70 | 62 | — | — | 70 | 65 | — | — |
| Toluene | — | — | 70 | 62 | — | — | 70 | 65 |
| Nitrocellulose ¼ sec | — | — | — | — | 10 | 10 | 10 | 10 |
| Interlaminar distance | 43 | 43 | 44 | 44 | 46 | 46 | 45 | 45 |

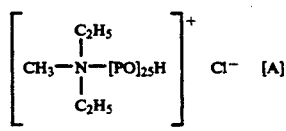

[A]

In the gel compositions of the principle of the present invention, the interlaminar distance was 43 to 46 Å, as shown in Table 1, which shows that even if there exists a cationic surfactant having a propylene oxide for which the organic modification of a clay mineral is difficult, it is possible to sufficiently increase the interlaminar distance of the organic modified clay mineral.

Accordingly, since it is possible to take a sufficient interlaminar distance in an organic modified clay mineral even in the presence of a cationic surfactant having a PO chain or an EO chain, the gel compositions of the present invention are inferred to have good thixotropy or gel property.

EXAMPLES 9 TO 24

Intermediates for a nail polish or coating were produced from the respective materials having the compositions shown in Table 2 by ordinary method using a two-stage rolling mill.

TABLE 2

|  | EXAMPLES |  |  |  |  |  |  |  |  |  |  |  |  |  |  |  | COMP |  |
|---|---|---|---|---|---|---|---|---|---|---|---|---|---|---|---|---|---|---|
|  | 9 | 10 | 11 | 12 | 13 | 14 | 15 | 16 | 17 | 18 | 19 | 20 | 21 | 22 | 23 | 24 | I | II |
| ① Benzyloctadecyldimethyl ammonium salt modified montmorillonite | 4 | 4 | 15 | 15 | 7 | 7 |  |  |  |  | 4 | 4 | 4 | 4 | 5 | 5 | 7 | 7 |
| Dioctadecyldimethyl ammonium salt modified montmorillonite |  |  |  |  |  |  | 10 | 10 | 7 | 7 |  |  |  |  |  |  |  |  |
| Octadecyltrimethyl ammonium salt modified montmorillonite |  |  |  |  |  |  |  |  |  |  | 4 | 4 |  |  |  |  |  |  |
| Hexadecyltrimethyl ammonium salt modified montmorillonite |  |  |  |  |  |  |  |  |  |  |  |  | 4 | 4 | 5 | 5 |  |  |
| ② Cation surfactant |  |  |  |  |  |  |  |  |  |  |  |  |  |  |  |  |  |  |
| B | 1 | 1 | 5 | 5 | 2 | 2 |  |  |  |  |  |  |  |  |  |  |  |  |
| C |  |  |  |  |  |  | 12 | 12 | 8 | 8 |  |  |  |  |  |  |  |  |
| D |  |  |  |  |  |  |  |  |  |  | 2 | 2 | 2 | 2 | 3 | 3 |  |  |
| E |  |  |  |  |  |  |  |  |  |  | 1 | 1 |  |  |  |  |  |  |
| F |  |  |  |  |  |  |  |  |  |  |  |  | 1 | 1 | 1 | 1 |  |  |

TABLE 2-continued

| | EXAMPLES | | | | | | | | | | | | | | | | COMP | |
|---|---|---|---|---|---|---|---|---|---|---|---|---|---|---|---|---|---|---|
| | 9 | 10 | 11 | 12 | 13 | 14 | 15 | 16 | 17 | 18 | 19 | 20 | 21 | 22 | 23 | 24 | I | II |
| G | | | | | | | | | | | | | | | | | 2 | |
| ③ Dipolyoxyethylene myristyl ethyl phosphoric acid | | 0.5 | | 2.5 | | 1 | | 6 | | 4 | | 1 | | 1 | | 1 | | 1 |
| Polyoxyethylenlauril ethel calboxylic acid | | | | | | | | | | | | 1 | | | | | | |
| Di-2-ethylhexyl sodium sulfosuccinate | | | | | | | | | | | | | | 1 | | | | |
| Polyoxyethylenlauryl sodium sulufonate | | | | | | | | | | | | | | | | 9 | | |
| ④ n-butyl acetate | 90 | 89.5 | 80 | 77.5 | 79 | 78 | | | | | 79 | 77 | 40 | 40 | 40 | 40 | 69 | 80 |
| Toluene | | | | | | | 78 | 72 | 70 | 66 | | | 39 | 37 | 39 | 29 | | |
| 99% ethanol | | | | | | | | | | | | | | | | | 10 | |
| ⑤ Nitrocellulose ½ sec | 5 | 5 | | | 12 | 12 | | 15 | 15 | 10 | 10 | 10 | 10 | 7 | 7 | 12 | 12 | |

The cationic surfactants shown in Table 2 are represented by the following formulas:

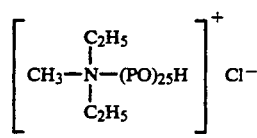

[B]

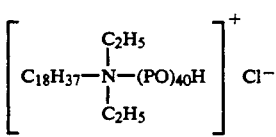

[C]

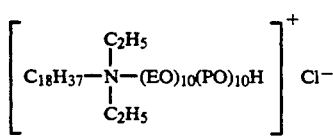

[D]

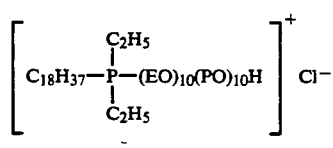

[E]

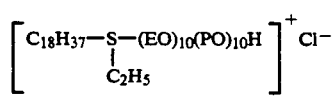

[F]

The cationic surfactant used in Comparative Example I was benzyloctadecylmethylammonium chloride having the following structure:

$$\left[ \begin{array}{c} CH_3 \\ | \\ C_{18}H_{37}-N-CH_2-C_6H_5 \\ | \\ CH_3 \end{array} \right]^+ Cl^- \quad [G]$$

In any of the gel compositions produced in Examples 9 to 24, the interlaminar distance of the organic clay mineral was not less than 40 Å, whereby the good thixotropy was confirmed.

In comparative Example I, benzyloctadecylmethylammonium chloride was used as the cationic surfactant. The nail polishes in Comparative Examples I and II had no problem at the point of the production.

In addition of a nitrocellulose is necessary as in the case of a nail polish, it is more preferable in the respect of dispersibility and the like to add a nitrocellulose in the stage of producing a gel composition as in Examples 9 and 10, not in the stage of producing the final product.

EXAMPLES 25 TO 38

The gel compositions (nail polishes) of the first and second aspects of the invention were produced by ordinary method and the age stability of each composition was examined.

The compositions of the respective materials and the properties of the gel compositions (nail polishes) are shown in Table 3.

TABLE 3-1

| | EXAMPLES | | | | | | | |
|---|---|---|---|---|---|---|---|---|
| | 25 | 26 | 27 | 28 | 29 | 30 | 31 | 32 |
| Nitrocellulose ½ sec | 14.5 | 14.5 | 15.0 | 15.0 | 12.6 | 12.6 | 15.0 | 15.0 |
| Alkyd resin | 10.0 | 10.0 | 2.0 | 2.0 | 5.0 | 5.0 | 5.0 | 5.0 |
| Acrylic resin | 10.0 | 10.0 | 8.0 | 8.0 | 5.0 | 5.0 | 2.0 | 2.0 |
| Acetyltributyl citrate | 5.0 | 5.0 | 5.0 | 5.0 | 5.0 | 5.0 | 8.0 | 8.0 |
| Isopropyl alcohol | 3.0 | 3.0 | 3.0 | 3.0 | 3.0 | 3.0 | 3.0 | 3.0 |
| n-butylacetate | 32.5 | 32.5 | 30.0 | 30.0 | 34.4 | 34.4 | 27.0 | 27.0 |
| Ethylacetate | 10.0 | 10.0 | 10.0 | 10.0 | 10.0 | 10.0 | 10.0 | 10.0 |
| n-butylalcohol | 3.0 | 3.0 | 3.0 | 3.0 | 3.0 | 3.0 | 3.0 | 3.0 |
| Pigment (red #202:titanium oxyde 1:1) | 1.0 | 1.0 | 1.0 | 1.0 | 1.0 | 1.0 | 1.0 | 1.0 |
| Pearl pigment | 1.0 | 1.0 | 3.0 | 3.0 | 1.0 | 1.0 | 1.0 | 1.0 |
| Example No. | No. 9 | No. 10 | No. 11 | No. 12 | No. 13 | No. 14 | No. 15 | No. 16 |
| Gel compositions content | 10.0 | 10.0 | 20.0 | 20.0 | 20.0 | 20.0 | 25.0 | 25.0 |
| Age stability | | | | | | | | |
| 1 month | ◉ | ◉ | ◉ | ◉ | ◉ | ◉ | ◉ | ◉ |
| 1 year | ◉ | ◉ | ◉ | ◉ | ◉ | ◉ | ◉ | ◉ |
| 2 years | ○ | ◉ | ○ | ◉ | ○ | ◉ | ○ | ◉ |
| Gloss of coating film | ◉ | ◉ | ◉ | ◉ | ◉ | ◉ | ◉ | ◉ |

TABLE 3-1-continued

|  | EXAMPLES | | | | | | | |
|---|---|---|---|---|---|---|---|---|
|  | 25 | 26 | 27 | 28 | 29 | 30 | 31 | 32 |
| Wearability | ⊚ | ⊚ | ⊚ | ⊚ | ⊚ | ⊚ | ⊚ | ⊚ |

TABLE 3-2

|  | EXAMPLES | | | | | | COMPARATIVE | |
|---|---|---|---|---|---|---|---|---|
|  | 33 | 34 | 35 | 36 | 37 | 38 | III | IV |
| Nitrocellulose ¼ sec | 11.25 | 11.25 | 13.0 | 13.0 | 13.0 | 13.0 | 12.6 | 12.6 |
| Alkyd resin | 3.0 | 3.0 | 5.0 | 5.0 | 5.0 | 5.0 | 5.0 | 5.0 |
| Acrylic resin | 2.0 | 2.0 | 5.0 | 5.0 | 5.0 | 5.0 | 5.0 | 5.0 |
| Acetyltributyl citrate | 2.0 | 2.0 | 5.0 | 5.0 | 5.0 | 5.0 | 5.0 | 5.0 |
| Isopropyl alcohol | 3.0 | 3.0 | 3.0 | 3.0 | 3.0 | 3.0 | 3.0 | 3.0 |
| n-butylacetate | 40.65 | 40.65 | 34.0 | 34.0 | 34.0 | 34.0 | 34.4 | 34.4 |
| Ethylacetate | 10.0 | 10.0 | 10.0 | 10.0 | 10.0 | 10.0 | 10.0 | 10.0 |
| n-butylalcohol | 3.0 | 3.0 | 3.0 | 3.0 | 3.0 | 3.0 | 3.0 | 3.0 |
| Pigment (red #202:titanium oxyde 1:1) | 0.1 | 0.1 | 1.0 | 1.0 | 1.0 | 1.0 | 1.0 | 1.0 |
| Pearl pigment | — | — | 1.0 | 1.0 | 1.0 | 1.0 | 1.0 | 1.0 |
| Example No. | No. 17 | No. 18 | No. 19 | No. 20 | No. 21 | No. 22 | I | II |
| Gel compositions content | 25.0 | 25.0 | 20.0 | 20.0 | 20.0 | 20.0 | 20.0 | 20.0 |
| Age stability | | | | | | | | |
| 1 month | ⊚ | ⊚ | ⊚ | ⊚ | ⊚ | ⊚ | □ | ▲ |
| 1 year | ⊚ | ⊚ | ⊚ | ⊚ | ⊚ | ⊚ | ▲ | ▲ |
| 2 years | ○ | ⊚ | ○ | ⊚ | ○ | ⊚ | ▲ | ▲ |
| Gloss of coating film | ⊚ | ⊚ | ⊚ | ⊚ | ⊚ | ⊚ | ▲ | ▲ |
| Wearability | ⊚ | ⊚ | ⊚ | ⊚ | ⊚ | ⊚ | ▲ | X |

As is clear from Table 3, the gel compositions (nail polishes) of the first and second aspects of the present invention were free of the precipitation of the pigments or the pearl pigment, excellent in age stability and had good film properties and application properties. Especially, the gel compositions (Examples 26, 28, 30, 32, 34, 36 and 38) with an anionic surfactant mixed therewith were excellent in a long-term age stability.

In contrast, the nail polishes (Comparative Examples III and IV) using the gel compositions obtained in Comparative Examples I and II, respectively, were in inferior in age stability, and about 1 month after, a supernatant solution is separated about the gel composition. With such deterioration of the gel property, the precipitation of the pigment or the pearl pigment was also observed, thereby greatly reducing the commercial value of the nail polishes.

When the nail polishes of Comparative Examples III and IV were actually used for manicure, the gloss of the coating film was bad and the coating film was easily peeled off the nails, in other words the wearability (resistance to peeling) was poor.

As is clear from Comparative Example III, the use of benzyloctadecylmethylammonium chloride as the cationic surfactant not only has no age stability improving effect but also greatly reduces the application properties. Thus, it is understood that all cationic surfactants do not exhibit the same effect but the use of a cationic surfactant having a PO chain or an EO chain specifically improves the age stability.

It is understood that Examples 26, 28, 30, 32, 34, 36 and 38 show that the existence of an anionic surfactant further improves the age stability, but that in Comparative Example IV which does not contain a cationic surfactant having a PO chain and/or an EO chain, the mere addition of an anionic surfactant rather exerts deleterious influence, namely, greatly lowers the age stability and the application properties.

It is therefore inferred from this fact that the presence of a cationic surfactant having a PO chain or an EO chain is essential for obtaining the age stability improving effect of an anionic surfactant.

The test for examining change in application property with time was next carried out, as shown in Table 4.

The nail polish obtained in Example 26 and a conventional nail polish were applied to 10 plastic nails, respectively, by double coating for each time. The change in application property with respect to the following number of times for application is shown.

TABLE 4

| COATING TIMES | EXAMPLE 26 | CONVENTIONAL NAIL POLISH |
|---|---|---|
| 1 | ○ | ○ |
| 2 | ○ | ○ |
| 3 | ○ | ○ |
| 4 | ○ | ○ |
| 5 | ○ | ○ |
| 6 | ○ | ○ |
| 7 | ○ | ○ |
| 8 | ○ | ○ |
| 9 | ○ | ○ |
| 10 | ○ | ○ |
| 11 | ○ | ▲ |
| 12 | ○ | ▲ |
| 13 | ○ | ▲ |
| 14 | ○ | ▲ |
| 15 | ○ | ▲ |

As is clear from Table 4, in the case of the conventional nail polish, the viscosity of the liquid began to increase at the 11th application, and the application property was deteriorated thereafter. In contrast, in the nail polish obtained in Example 26, almost the same application property as at the first application was obtained even after the 15th application.

Figure 2:
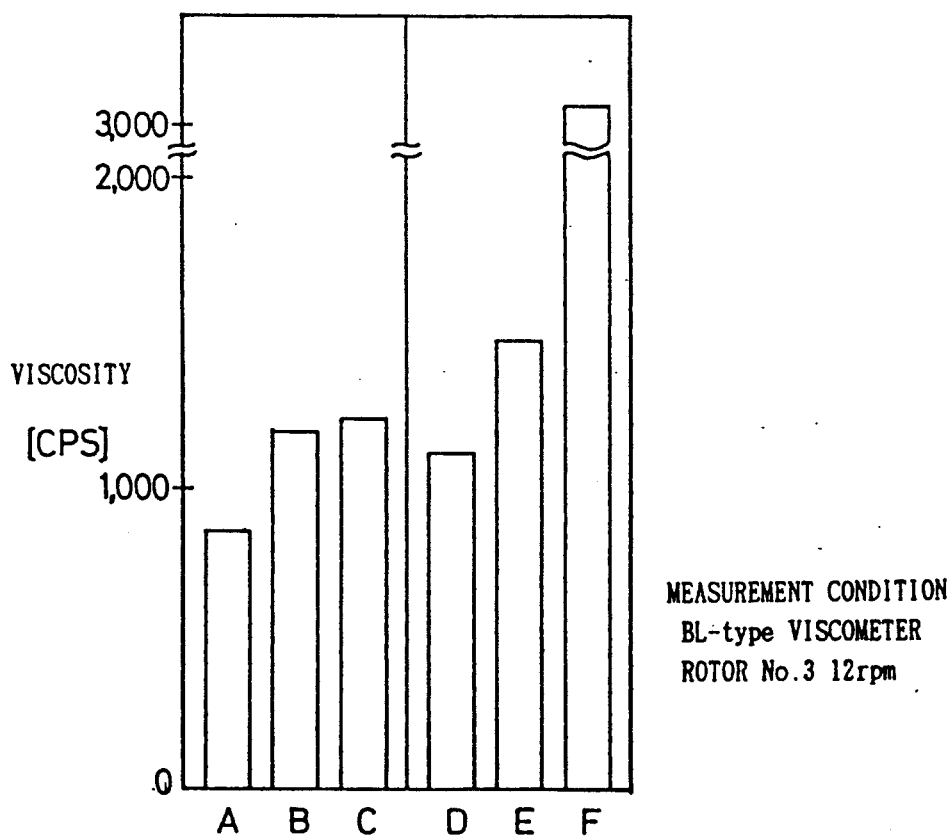
FIG. 2 is an explanatory view of the change in viscosity of a nail polish in accordance with the present invention and a conventional nail polish in various states.
Figure 3:
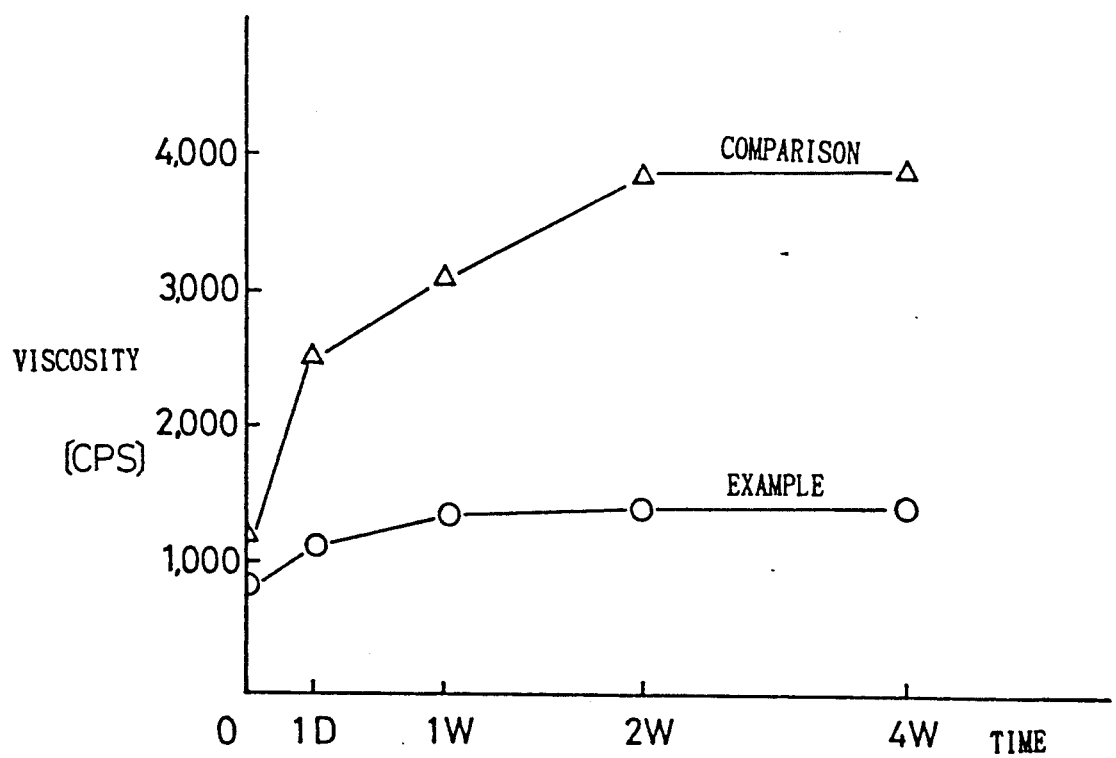
FIG. 3 is an explanatory view of the change in viscosity with time of a conventional nail polish and a nail polish in accordance with the present invention.

Such improvement of application property is also proved from FIGS. 2 and 3.

FIG. 2 shows the change in the viscosity of the nail polish obtained in Example 26 and a conventional one in various states. FIG. 2(A) shows the viscosity of the nail polish of Example 26 one hour after the production, which is about 800 cps. FIG. 2(B) shows the viscosity of the nail polish of Example 26 with the solvent evaporated so as to raise the solid content by 3%. It is understood that although the viscosity rises, it is limited to about 1,200 cps.

FIG. 2(C) shows the viscosity of the nail polish of Example 26 one week after the production. There is little difference between the viscosity of the nail polish shown in FIG. 2(B) and that shown in FIG. 2(C).

In contrast, FIG. 2(D) shows the viscosity of the conventional nail polish one hour after the production, which is about 1,200 cps. FIG. 2(E) shows the viscosity of the conventional nail polish with the solvent evaporated in correspondence with the nail polish shown in FIG. 2(B). It is understood that the viscosity of the conventional nail polish rises to about 1,500 cps. FIG. 2(F) shows the viscosity of the conventional nail polish one week after the production, which corresponds to the nail polish shown in FIG. 2(C). The viscosity of the conventional nail polish rises to about 3,000 cps.

FIG. 3 shows the change in the viscosity with time of the nail polish of Example 26 and a conventional one. The viscosity of the nail polish of Example 26, which is 800 cps at the initial stage, rises to about 1,200 cps one week after and scarcely changes thereafter.

In contrast, the viscosity of the conventional nail polish rises to about 2 times of the initial value in about one day and keeps rising for about two weeks. The viscosity of thereof two weeks after is not less than 3 times of the initial value.

Therefore, it is expected that the quality of the conventional nail polish as a commercial product greatly changes in accordance with the period for display, and the control thereof is very difficult.

From these experiments, it is understood that in the nail polish of Example 26 and the conventional one having substantially the same viscosity immediately after the production, that when the solvent is evaporated, the viscosity of the conventional one has a slightly stronger tendency to rise, and that one week after the production, the viscosity of the conventional one rises so much as to deteriorate the application property, while the nail polish of Example 26 has almost the same viscosity.

As described above, according to the nail polish of Example 26, the viscosity scarcely changes even if the solvent is reduced (the solid content is increased), as shown in Table 4 and FIG. 2(B). Accordingly, even if the solvent is gradually evaporated in actual continuous use of the nail polish, the viscosity thereof is maintained substantially at a constant value, thereby securing a good application property.

In contrast, the viscosity of the conventional nail polish rapidly changes even when it is only allowed to stand, as shown in FIGS. 2(C), 2(F) and 3. Since the period from the production of a nail polish to actual use thereof is indefinite, the application property of the conventional nail polish is sometimes deteriorated. On the other hand, the viscosity of the nail polish of Example 26 scarcely changes one week after the production. Thus, according to the present invention, even if the period from the production of a nail polish to actual use thereof is greatly varied, it is possible to provide a nail polish having a constant application property.

EXAMPLES 39 TO 46

The gel compositions (coatings) of the first and second aspects of the invention were produced by ordinary method by using the gel compositions obtained in Examples 9 to 46. The compositions of the respective materials and the properties of the gel compositions (coatings) are shown in Table 5.

TABLE 5

| | EXAMPLES | | | | | | | |
|---|---|---|---|---|---|---|---|---|
| | 39 | 40 | 41 | 42 | 43 | 44 | 45 | 46 |
| BECCOZOL 1308*1 | 45.0 | 45.0 | 38.0 | 38.0 | 50.0 | 50.0 | 35.0 | 35.0 |
| SUPERBECCAMINJ-820*2 | 20.0 | 20.0 | 20.0 | 20.0 | 20.0 | 20.0 | 20.0 | 20.0 |
| SOLUVENTS #150*3 | 2.0 | 2.0 | 4.0 | 4.0 | 2.0 | 2.0 | 2.0 | 2.0 |
| Butylcellosolve | 12.5 | 12.5 | 10.0 | 10.0 | 10.0 | 10.0 | 5.0 | 5.0 |
| n-butanol | 2.0 | 2.0 | 4.0 | 4.0 | 2.0 | 2.0 | 2.0 | 2.0 |
| Pearl pigment | 5.0 | 5.0 | — | — | — | — | 20.0 | 20.0 |
| Titanium oxide | 10.0 | 10.0 | 6.0 | 6.0 | 10.0 | 10.0 | 5.0 | 5.0 |
| Lactimon ®*4 | 0.2 | 0.2 | 0.1 | 0.1 | 0.2 | 0.2 | 0.1 | 0.1 |
| BYK ®-300*5 | 0.2 | 0.2 | 0.2 | 0.2 | 0.2 | 0.2 | 0.2 | 0.2 |
| Dibutylphthalate | 0.6 | 0.6 | 0.7 | 0.7 | 0.6 | 0.6 | 0.7 | 0.7 |
| Example No. | No. 9 | No. 10 | No. 15 | No. 16 | No. 17 | No. 18 | No. 23 | No. 24 |
| Gel composition content | 2.5 | 2.5 | 17.0 | 17.0 | 5.0 | 5.0 | 10.0 | 10.0 |
| Age stability | | | | | | | | |
| 1 month | ⊚ | ⊚ | ⊚ | ⊚ | ⊚ | ⊚ | ⊚ | ⊚ |
| 1 year | ⊚ | ⊚ | ⊚ | ⊚ | ⊚ | ⊚ | ⊚ | ⊚ |
| 2 years | ○ | ⊚ | ○ | ⊚ | ○ | ⊚ | ○ | ⊚ |
| Gloss of coating film | ⊚ | ⊚ | ⊚ | ⊚ | ⊚ | ⊚ | ⊚ | ⊚ |
| Wearability | ⊚ | ⊚ | ⊚ | ⊚ | ⊚ | ⊚ | ⊚ | ⊚ |

*1,*2 NIHON LAIHIHOLD INC.
*3 ESSO STANDERD INC.
*4,*5 BIC CHEMY INC.

As is clear form Table 5, the gel compositions (coatings) of the first and second aspects of the present invention were free of the precipitation of the pigments or the pearl pigment, excellent in age stability and had good film properties and application properties. Especially, the gel compositions (Examples 40, 42, 44 and 46) with an anionic surfactant mixed therewith were excellent in a long-term age stability.

EXAMPLES 47 AND 48, COMPARATIVE EXAMPLES V AND VI

Table 6 shows the examples and comparative examples of gel compositions (nail polishes) of the first and second aspects of the present invention. The gel composition production No. in Table 6 represents the gel composition production having the composition and produced by the process of the corresponding gel composition production No. shown in Table 7.

TABLE 6

|  | CONPARATIVE | | EXAMPLES | |
|---|---|---|---|---|
|  | V | VI | 47 | 48 |
| Nitrocellulose/4 | 12.6 | 12.6 | 12.6 | 12.6 |
| Alkyd resin | 5.0 | 5.0 | 5.0 | 5.0 |
| Acrylic resin | 5.0 | 5.0 | 5.0 | 5.0 |
| Acetyltributyl citrate | 5.0 | 5.0 | 5.0 | 5.0 |
| Isopropyl alcohol | 3.0 | 3.0 | 3.0 | 3.0 |
| n-butylacetate | 34.4 | 34.4 | 34.4 | 33.7 |
| Ethylacetate | 10.0 | 10.0 | 10.0 | 10.0 |
| n-butanol | 3.0 | 3.0 | 3.0 | 3.0 |
| Pigment | 1.0 | 1.0 | 1.0 | 1.0 |
| Pearl Pigment | 1.0 | 1.0 | 1.0 | 1.0 |
| Cation surfactant H | — | — | — | 0.2 |
| Dipolyoxymyristyl ethyl phosphoric acid | — | — | — | 0.4 |
| Di-2-etylsulphonic sodium succinate | — | — | — | 0.1 |
| Gel composition No. | No. 1 | No. 2 | No. 3 | No. 1 |
| Gel composition content | 20.0 | 20.0 | 20.0 | 20.0 |
| Age stability | | | | |
| 1 month | ⊚ | ⊚ | ⊚ | ⊚ |
| 1 year | □ | □ | ⊚ | ⊚ |
| 2 years | □ | □ | ○ | ⊚ |
| Gloss of coating film | ○ | ○ | ⊚ | ⊚ |
| Wearability | ○ | ○ | ⊚ | ⊚ |

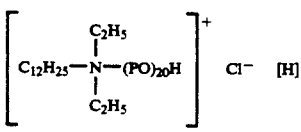

TABLE 7

|  |  | Gel composition No. | | |
|---|---|---|---|---|
|  |  | 1 | 2 | 3 |
| ① | Benzyldimethyl octadecylammonium salt modified montmorillonite | 9.0 | 9.0 | 9.0 |
| ② | Diphenylsilane | 6.0 | — | — |
|  | Polypropyleneglycol (M.W. 2,700) | 3.0 | — | — |
|  | Acetyltributyl citrate | — | 9.0 | 9.0 |
| ③ | Nitrocellulose ¼ sec | 12.0 | 12.0 | 12.0 |
| ④ | n-butyl acetate | 70.0 | 30.0 | 29.7 |
|  | Toluene | — | 40.0 | 40.0 |
| ⑤ | Cation surfactant I | — | — | 0.3 |

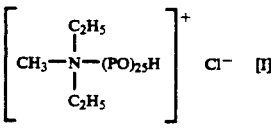

Process

A gel composition was produced by dipping the chips obtained by rolling a mixture of the materials (1) to (3) by a two-stage heating rolling mill into the solvent (4) so as to swell the chips and dispersing the chips sufficiently.

In the gel composition production No. 3, the material 5 was further added to the chips and thereafter the chips were dispersed.

As is clear from Table 6, the gel compositions (coatings) of the first and second aspect of the present invention were free of the precipitation of the pigments or the pearl pigment, excellent in age stability and had good film properties and application properties. Especially, the gel composition 48 of the second aspect with an anionic surfactant mixed therewith was excellent in a long-term age stability.

EXAMPLE 49 AND COMPARATIVE EXAMPLE VII

Table 6 shows the example and comparative examples of gel compositions (nail polishes) of the second aspect of the present invention. The gel composition production No. in Table 6 represents the gel composition production having the composition and produced by the process of the corresponding gel composition production No. shown in Table 7.

TABLE 8

|  | CONPARATIVE VII | EXAMPLE 49 |
|---|---|---|
| BECCOZOL1308*1 | 50.0 | 50.0 |
| SUPERBECCAMINJ-820*2 | 20.0 | 20.0 |
| SOLUVETUN#150*3 | 3.0 | 3.0 |
| Butyl cellocolve | 8.0 | 7.75 |
| n-butanol | 3.0 | 3.0 |
| Titanium oxide | 10.0 | 10.0 |
| Lactimon ®*4 | 0.1 | 0.1 |
| Byk ®-300*5 | 0.2 | 0.2 |
| Dibutylphthalate | 0.7 | 0.7 |
| Cation surfactant J | — | 0.1 |
| Dipolyoxyethylene (2 mol add)myristyl ethyl phosphate | — | 0.1 |
| Di-2-ethylenhexyl sodium sulphosuccinate | — | 0.05 |
| Gel composition No. | No. 2 | No. 2 |
| Gel composition content | 5.0 | 5.0 |
| Age stability | | |
| 1 month | ⊚ | ⊚ |
| 1 year | □ | ⊚ |
| 2 years | □ | ⊚ |
| Gloss of corting film | ○ | ⊚ |
| wearability | ○ | ⊚ |

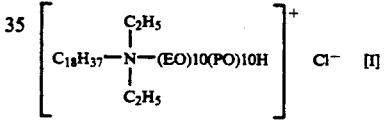

*1, *2 NIHON LAIHIHOLD INC.
*3 ESSO STANDERD INC.
*4, *5 BIC CHEMY INC.

As is clear from Table 8, the gel composition (coating) of the second aspect of the present invention was free of the precipitation of the pigments or the pearl pigment over more than two years, and excellent in age stability and had good film properties and application properties.

In contrast, in Comparative Example VII, precipitation or the like was observed one year after the production, and the age stability was not very good.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. A gel composition comprising, as essential components, a cationic surfactant having PO chain and/or an EO chain represented by the following general formulas:

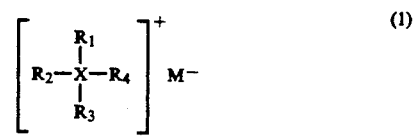

ene oxide chain represented by the following general formulas:

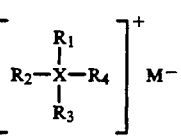
(1)

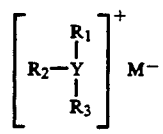
(2)

wherein X represents nitrogen or phosphorus, Y is sulfur, $M^-$ is chlorine ion, bromine ion, iodine ion, nitrous acid ion, hydroxyl ion, acetic acid ion, methyl sulfate ion or a combination thereof, $R_1$ is a hydrocarbon group having 1 to 30 carbon atoms with or without a substituent, and at least one of $R_2$, $R_3$ and $R_4$ represents a hydrocarbon group having 1 to 30 carbon atoms and a PO chain and/or an EO chain with or without hydrogen or a substituent at the end of the hydrocarbon group, and the remaining $R_2$, $R_3$ and $R_4$ groups being a hydrocarbon group having 1 to 30 carbon atoms with or without the same or different substituents;

an organic modified clay mineral, said mineral being modified by a quaternary ammonium salt cation surfactant represented by the following general formula

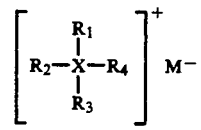

wherein $R_1$ represents an alkyl group having 10 to 22 carbon atoms or a benzyl group, $R_2$ is a methyl group or an alkyl group having 10 to 22 carbon atoms, each of $R_3$ and $R_4$ is an alkyl group having 1 to 3 carbon atoms or a hydroxyalkyl group and M is a halogen atom or a methyl sulfate residue;
a solvent;
and a pigment.

7. A gel composition according to claim 1, wherein the number of addition moles of the PO chain and/or the EO chain is 1 to 50.

8. A gel composition according to claim 7 wherein the number of addition moles is 9 to 40.

* * * * *

-continued

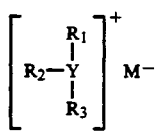
(2)

wherein X represents nitrogen or phosphorus, Y is sulfur, $M^-$ is chlorine ion, bromine ion, iodine ion, nitrous acid ion, hydroxyl ion, acetic acid ion, methyl sulfate ion or a combination thereof, $R_1$ is a hydrocarbon group having 1 to 30 carbon atoms with or without a substituent, and at least one of $R_2$, $R_3$ and $R_4$ represents a hydrocarbon group having 1 to 30 carbon atoms and a PO chain and/or an EO chain with or without hydrogen or a substituent at the end of the hydrocarbon group and the remaining $R_2$, $R_3$ and $R_4$ groups being a hydrocarbon group having 1 to 30 carbon atoms with or without the same or different substituents;

an organic modified clay mineral, said mineral being modified by a quaternary ammonium salt cation surfactant represented by the following general formula

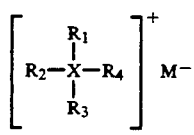

wherein $R_1$ represents an alkyl group having 10 to 22 carbon atoms or a benzyl group, $R_2$ is a methyl group or an alkyl group having 10 to 22 carbon atoms, each of $R_3$ and $R_4$ is an alkyl group having 1 to 3 carbon atoms or a hydroxyalkyl group and M is a halogen atom or a methyl sulfate residue;
and a solvent.

2. A gel composition according to claim 1, further containing a powder pigment.

3. A gel composition according to claim 1, further containing an anionic surfactant.

4. A gel composition according to claim 3, wherein the anionic surfactant is a phosphoric acid ester, a carboxylic acid, a sulfonic acid or a sulfuric acid ester.

5. A gel composition according to claim 1, further containing nitrocellulose.

6. A nail polish comprising at least one cationic surfactant having a propylene oxide chain and/or an ethyl-